United States Patent
Thomas et al.

(10) Patent No.: US 9,989,360 B2
(45) Date of Patent: Jun. 5, 2018

(54) METHOD FOR ESTIMATING ELEVATION CHANGES TRAVELED BY A USER

(71) Applicant: Withings, Issy les Moulineaux (FR)

(72) Inventors: Rémi Thomas, Vanves (FR); Eric Carreel, Meudon (FR)

(73) Assignee: WITHINGS, Issy les Moulineaux (FR)

(*) Notice: Subject to any disclaimer, the term of this patent is extended or adjusted under 35 U.S.C. 154(b) by 686 days.

(21) Appl. No.: 14/534,977

(22) Filed: Nov. 6, 2014

(65) Prior Publication Data

US 2015/0127296 A1   May 7, 2015

(30) Foreign Application Priority Data

Nov. 7, 2013  (FR) .................................. 13 60909

(51) Int. Cl.
| | |
|---|---|
| G06F 19/00 | (2018.01) |
| G01C 5/00 | (2006.01) |
| G01C 22/00 | (2006.01) |
| A61B 5/11 | (2006.01) |
| G01C 5/06 | (2006.01) |
| A61B 5/00 | (2006.01) |

(52) U.S. Cl.
CPC .............. G01C 5/00 (2013.01); A61B 5/1118 (2013.01); G01C 5/06 (2013.01); G01C 22/006 (2013.01); *A61B 5/6801* (2013.01)

(58) Field of Classification Search
CPC ..... G01P 15/0891; G01P 3/50; A63B 71/0605
USPC .......................................... 702/150, 182–185
See application file for complete search history.

(56) References Cited

U.S. PATENT DOCUMENTS

| | | | |
|---|---|---|---|
| 5,295,085 A | 3/1994 | Hoffacker | |
| 6,539,336 B1* | 3/2003 | Vock | A42B 3/0433 |
| | | | 702/178 |

FOREIGN PATENT DOCUMENTS

| | | |
|---|---|---|
| DE | 10 2008 049750 A1 | 4/2010 |
| EP | 2 083 244 A1 | 7/2009 |
| WO | 2013/136251 A1 | 9/2013 |

OTHER PUBLICATIONS

French Search Report and Written Opinion issued in related to French Patent Application No. 13 60909; dated Nov. 7, 2013.

* cited by examiner

*Primary Examiner* — Edward Raymond
(74) *Attorney, Agent, or Firm* — Miller, Matthias & Hull LLP

(57) ABSTRACT

A method for estimating the elevation change traveled by a user, said method using a pressure sensor and a temperature sensor, the pressure sensor being adapted to be held fixed to the user, the method comprising:
  a)—an operation of periodically sampling raw pressure values, reading the current raw pressure at a first sampling frequency, the raw values being stored in the form of pressure or the corresponding altitude in a first buffer (B1),
  b)—a filtering operation based on the raw values stored in the first buffer, in order to determine filtered values,
  c)—a variance calculation, performed on at least a portion of the filtered values, in order to determine a condition for including the elevation changes corresponding to the observed pressure or altitude differences.

15 Claims, 3 Drawing Sheets

METHOD FOR ESTIMATING ELEVATION CHANGES TRAVELED BY A USER

CROSS-REFERENCE TO RELATED APPLICATION

This application claims priority under the Paris Convention to French Patent Application No. 13 60909 filed on Nov. 7, 2013.

FIELD OF THE DISCLOSURE

The present invention relates to methods for estimating elevation changes traveled by a user.

BACKGROUND OF THE DISCLOSURE

More particularly, the invention relates to a method for estimating the elevation change traveled by a user, by means of a device intended to be worn or carried by the user, said device being adapted to measure the ambient pressure and deduce the corresponding altitude from it. The measurement of pressure changes allows deducing the corresponding change in altitude and consequently deducing an elevation change traveled by the user.

Document US 2012084053 describes a device for monitoring and recording a user's movement, and in particular for determining elevation changes traveled by that user. However, the estimation method applied in this document uses an algorithm based on threshold filters and hysteresis mechanisms.

Such an algorithm can be skewed by one-time anomalous values that can lead to unwanted inclusion as a change, especially if the device containing the pressure sensor is subjected to the acoustic phenomena that can occur when an individual enters a room, opens a door, takes the elevator, or is in a vehicle that enters and exits a tunnel. Moreover, such an algorithm requires significant computing power and memory capacity.

There is therefore a need to provide an improved method for filtering the pressure values measured or converted into altitude values, so as to eliminate the anomalous values while providing the elevation changes traveled in near real-time, but where the method does not require too much computing power.

Throughout this application, the term "buffer" will be used to refer to buffer memory storage.

SUMMARY OF THE DISCLOSURE

For this purpose, the invention proposes a method for estimating the elevation change traveled by a user, said method using at least one pressure sensor adapted to provide pressure values and a temperature sensor adapted to provide temperature values in order to adjust the pressure values, said pressure sensor being adapted to be held substantially fixed to at least a portion of the body of said user during the implementation of said method, said method comprising at least:
- an operation of periodically sampling raw pressure values, reading the current raw pressure at a first sampling frequency $F_1$, the raw values being stored in the form of pressure or the corresponding altitude in a first buffer,
- a filtering operation based on the raw values stored in the first buffer, in order to determine filtered values (pressure or corresponding altitude),
- a variance calculation, performed on at least a portion of the filtered values, in order to determine a condition for including the elevation changes corresponding to the observed pressure or altitude differences,
- an elevation change traveled calculation, particularly the positive elevation change, by the user during his/her displacement.

With these arrangements, such a condition for including elevation changes based on the variance calculation eliminates potentially anomalous values; the steps of subsampling-filtering-variance calculation allow obtaining a reliable estimate of the elevation change in near real-time from the values actually measured, and at the same time eliminating any pressure values that are anomalous or correspond to an interfering acoustic phenomenon. In addition, the variance calculation step is an optimal criterion for discriminating between true upward or downward travel from possible disruptions of pressure signals. In addition, the proposed method is less demanding in terms of computing power and memory, which is advantageous for a very small embedded device.

In preferred embodiments of the invention, one or more of the following arrangements may possibly be used:
- the filtering operation is performed at the rate of the first sampling frequency $F_1$, so that the filtering operation is synchronous with the sampling operation.
- the variance calculation is performed at a second frequency $F_2$, lower than the first, so that the computational load involved is relatively limited and in addition the variance calculation frequency is spaced further apart which limits the rate of erroneous inclusions.
- the first frequency $F_1$ is a multiple of the second frequency $F_2$, whereby the clock of the second frequency $F_2$ may be easily obtained from the basic clock of the first frequency $F_1$.
- the variance calculation is performed on subsampled filtered values (P values) stored in a second buffer, so that the most complex calculation, namely the variance calculation, works with a limited number of values.
- the method further comprises the following step:
the result of the variance calculation VAR is compared to a predetermined threshold value S:
  - if VAR>S then the inclusion condition is 'true' and the observed elevation changes are included in the calculation of the elevation change estimate,
  - if VAR<S then the inclusion condition is 'false' and the observed elevation changes are not included in the calculation of the elevation change estimate. whereby the inclusion of the elevation changes is done intelligently, and possible noise contaminating the pressure signals is eliminated.
- when the inclusion condition changes from 'false' to 'true', the included elevation change is based on the oldest value stored in the second buffer, so that despite the presence of the delay-introducing filter, there is substantially no loss of elevation changes in the calculation.

The invention further provides a device adapted to implement the method. The invention also provides a device in the form of a personal activity monitoring unit.

BRIEF DESCRIPTION OF THE DRAWINGS

Other features and advantages of the invention will be apparent from the following description of one of its embodiments, given by way of non-limiting example, with reference to the accompanying drawings.

In the drawings.

DETAILED DESCRIPTION OF THE DISCLOSURE

In the various figures, the same references denote identical or similar elements.

Figure 1:
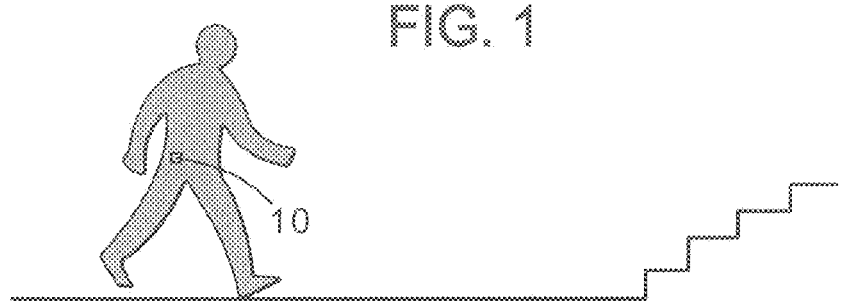
FIG. 1 represents a person wearing a device implementing the method of the invention.
Figure 2:
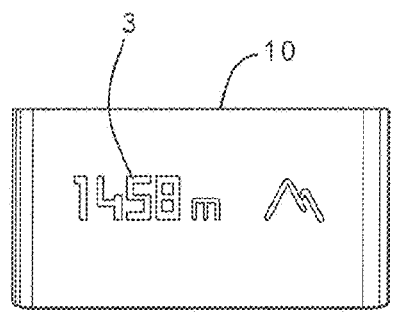
FIG. 2 represents a personal activity monitor as being the form of the device implementing the method of the invention.

In FIG. 1, a user is wearing a device 10 intended to indicate elevation changes he or she travels. The device 10 can detect the elevation changes it undergoes while the user is wearing said device 10. In the example illustrated in FIG. 2, the device 10 is in the form of a personal activity monitor able to inform the user of his or her physical activity, walking, running, sleeping, climbing stairs, etc. The elevation change estimation device 10 is for example in the form of a unit including a display system for displaying the elevation changes traveled by the user, said elevation changes being determined by the method implemented by the device 10. According to one embodiment (not shown), the device 10 may be an integral part of an advanced mobile phone known as a smartphone.

Figure 3:
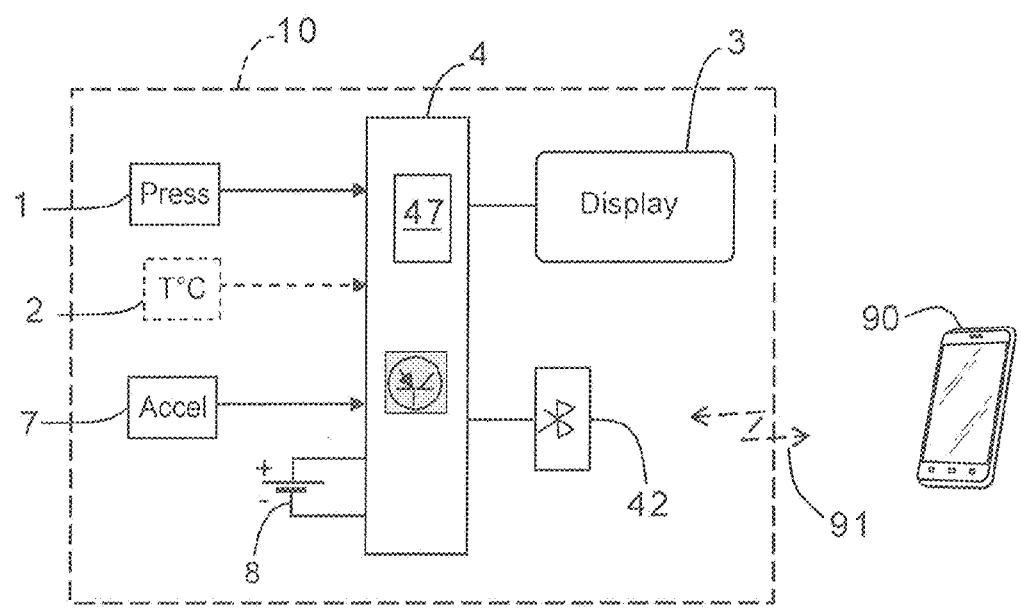
FIG. 3 represents a block diagram of a device implementing the method of the invention.

The device 10, whose principle is illustrated in FIG. 3, comprises for example at least one pressure sensor 1 and a temperature sensor 2. The pressure sensor 1 is adapted to provide pressure values. The temperature sensor is adapted to provide temperature values in order to adjust the pressure values. The measured pressure values may for example be correlated via a nomogram to the observed temperature values, and adjusted accordingly.

The device 10 (and particularly the pressure sensor it contains) is for example adapted to be held substantially fixed to at least a portion of the body of said user during the implementation of said method, for example worn on the user's belt (see FIG. 1) or on a band secured to the user's wrist. It may also be integrated into a smartphone type of device carried by the user, or even in an earpiece.

The device 10 comprises a processing unit (CPU) 4 to which the temperature 1 and pressure 2 sensors are connected. Also provided is a multi-axis accelerometer 7 for detecting accelerations experienced by the device, which are used to estimate the accelerations experienced by the user. The acceleration information can be used to differentiate the elevation changes physically climbed from those relating to a mechanical ascension such as an elevator for example.

The CPU 4 comprises a display 3 configured to make a plurality of information items available to the user and in particular a meter of positive elevation gains (ascending). This meter may be reset daily or at some other interval, depending on the configuration specified by the user.

The CPU 4 processes the values via a processor that includes a memory area 47 having buffers whose usefulness will be described below.

The CPU 4 controls the display system 3 and/or communicates via a Bluetooth™ communication interface 42 with a smartphone 90, via an interaction of values 91. A complementary display may be provided on the smartphone 90 and/or a configuration management by a smartphone application linked to the activity monitor.

The CPU 4 is powered by an embedded power source 8, for example a rechargeable battery as is the case here. This battery powers all the elements embedded in the device, meaning the sensors 1, 2, 7, the display 3, and the CPU 4.

The method may be carried out either based on the pressure values or after conversion of the pressure values into altitude values. This conversion can be done at any stage of the method, using the relation:

$$p(z) = 1013.25 * \left(1 - \frac{0.0065 * z}{288.15}\right)^{5.255}$$

p indicating the atmospheric pressure, z indicating the altitude above the average sea level. It is evident here that with the one-to-one relationship between altitude and pressure, it is possible to work with either the altitude or the pressure.

In a preferred embodiment of the invention, the conversion of pressure values to altitude values takes place when the values are sampled, and it is the raw altitude and not raw pressure values that are stored in the buffers.

In the rest of what follows, the most general case for the values will be considered, whether they are pressure or altitude values.

In a preferred embodiment of the invention, the method is implemented in the following steps:

An operation of periodically sampling raw values is performed. The raw values are collected at a first sampling frequency F1, then stored in a first buffer B1. Said first buffer B1 contains for example N memory locations. The first frequency F1 can be 1 Hz for example (therefore one clock pulse every second).

The raw values are continuously renewed with new values which are sampled over time. Each new sampled value is placed in the last occupied memory location, which is the Nth, the other values are shifted towards the first memory location, and the value that was contained in the first occupied location is lost and therefore replaced by the one that had been in the second occupied location just before the latest capture (principle of the sliding window).

At the same first frequency F1, which corresponds to clock ticks spaced apart by a period T1 where T1=1/F1, a filter is applied to the set of values contained in the first buffer B1. In other words, at each clock tick a filter is applied to the set of values contained in the first buffer B1 at that moment. For example, this can be a median filter FM which takes the median of the set of values contained in the first buffer B1 at the time the filter is applied. It could also concern another type of filter.

Figure 4:
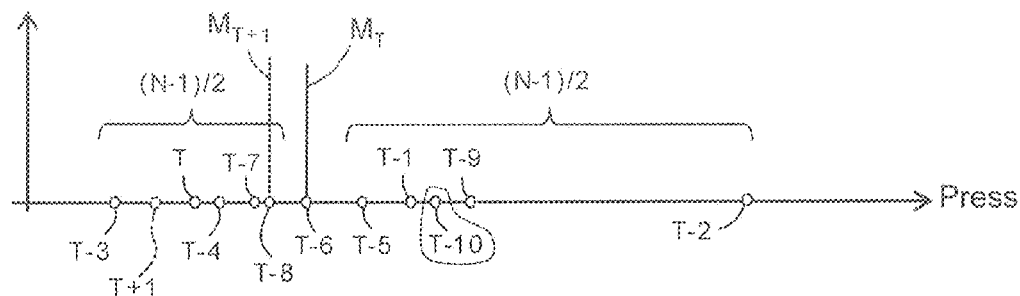
FIG. 4 illustrates a median filter, FIG. 5 schematically represents the two buffers used in the method.

The case of a median filter FM is illustrated in FIG. 4. When applied to the N values stored in the first buffer B1, N being odd, the N values are ordered and the actually measured value that has as many values below it (N−1)/2 as values above it (N−1)/2 is chosen as the median.

The median filter FM can also be applied to an even number of values. In this case, the set of N values is divided into two subsets of N/2 values and the median value is the one of the actually measured values that is between the maximum value of the lower subset and the minimum value of the upper subset.

The use of a median filter FM means there is a delay in observing an elevation change. When the raw values collected are trending towards higher values for example, several new readings will be required before the median value is equivalently shifted. The use of a median filter FM eliminates anomalous value(s) resulting from a short-lived acoustic phenomenon.

The values filtered in this manner are then subsampled at the second frequency F2, preferably a multiple of the first frequency F1, and the values selected by the subsampling are stored in a second buffer B2.

A variance calculation is then performed using these subsampled filtered values. The variance calculation therefore uses at least a portion of the filtered values. The subsampling reduces the number of values used for the variance calculation, and so reduces the computing power required.

The second buffer B2 may contain more or fewer values than the first buffer B1. Let us consider a second buffer B2 that has P availability. The sampled values stored in the second buffer B2, numbering P, are therefore regularly replaced. For each new value subsampled from the first buffer B1, said new value is integrated into the second buffer B2, the set of values contained in the second buffer B2 are shifted towards the first value stored in the second buffer B2, and the oldest value stored in the second buffer B2 is discarded.

The variance is given by the following relation:

$$VAR = \frac{1}{P-1} \sum_{i=1}^{P} (xi - \bar{x})^2$$

where xi are the values contained in the second buffer B2 and where $\bar{x}$ is the average of the xi.

The variance calculation in this embodiment is therefore done on the second buffer B2 at the second frequency F2, meaning each time the second buffer B2 is updated. The second frequency F2 corresponds to a clock which pulses at a period T2. The variance calculation is therefore performed using values stored in the second buffer B2 at the moment of the clock tick.

The scaling factor between the first frequency F1 and the second frequency F2 may for example be selected by the user.

The delay due to filtering the raw values therefore affects the value of the variance which is calculated from the subsampled filtered values. The storage capacity of the second buffer B2 is adapted to allow storing sufficient sampled values to enable delayed calculation of the elevation change.

In the most general case, the variance calculation allows defining a condition for the inclusion or non-inclusion of the corresponding elevation changes observed.

The variance is used to determine whether a true elevation change has been traveled by the user.

The value of the variance VAR is for example compared to a threshold S.

If the value of the variance VAR is below the threshold S, then the inclusion condition is 'false' and the elevation changes observed are not included in the calculation of the elevation change estimate.

If the value of the variance VAR is above the threshold S, then the inclusion condition is 'true' and the elevation changes observed are included in the calculation of the elevation change estimate.

In the most general case, when the variance is greater than the threshold and an elevation change has been traveled, the elevation change achieved is estimated by calculating the difference D between the last two successive sampled filtered values stored in the buffer B2.

A special situation can be isolated for the first time that the variance VAR exceeds the threshold S. The elevation change is estimated for example by calculating the difference between the last sampled filtered value stored in buffer B2, and the oldest value stored in the second buffer B2. It may also concern the difference between the last sampled filtered value stored in the second buffer B2, and an older value stored in the second buffer B2.

The value of the elevation change estimated in this manner makes up for the delay in capturing information on elevation changes arising from the delay in the variance estimation due to using sampled filtered values (see above). An elevation change will therefore be detected after a delay, via the variance VAR, and this delay in detection can be offset by evaluating the elevation change using the oldest values in the second buffer B2. This later correction or compensation will be more or less precise depending on the storage capacity of the second buffer B2 and on the choice of the second value used in finding the difference.

The variance VAR may temporarily spike above the threshold without corresponding to a true change in the trend. This can also be corrected by the fact that the first time the variance rises above the threshold the difference is found between an old value in the second buffer B2 and the last value saved in the second buffer B2. The difference between these two outliers helps to discriminate between a variance that that has actually crossed the threshold and a temporary spike.

If the difference D is positive, the elevation change is considered to be upward and is stored in a first counter C1, to be combined with the other retained values. This is the value of interest to a user who wishes to obtain an estimate of his or her upward travel.

If the difference D is negative, the elevation change corresponds to downward travel and is stored in a second counter C2. In one embodiment of the invention, this second counter C2 will allow verifying the validity of the measured upward travel by being able to verify that, for a return to a starting point, the sum of the upward and downward travel yields an elevation change of zero.

When the variance VAR falls below the threshold S, the elevation change is considered to be zero and no counter is incremented.

When there is a sudden reversal in the trend, from upward to downward for example, the variance VAR remains above the threshold S but the difference D between successive values changes from a positive difference to a negative difference. In this case at least three values will be collected and the differences determined before confirming the return to downward travel. After confirmation, the downward travel will be established as starting from the first value initially suspected of being a return to downward travel.

In the initial state, all buffers are empty. When the first three values are collected by the detector, the median is calculated and the set of values contained in the first buffer B1 is filled/overwritten with this value. Next, new values are collected and entered into the first buffer B1 and then the conventional method as described above continues. The same occurs for all values of the second buffer B2.

Figure 5:
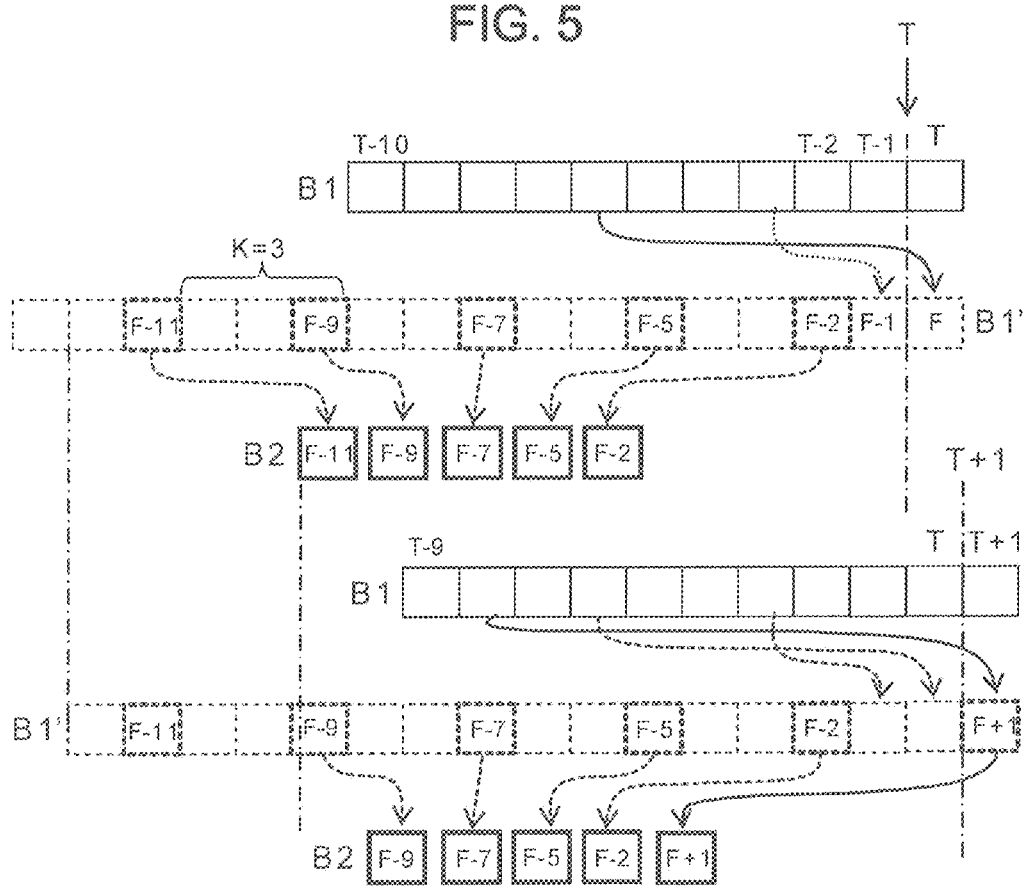

More specifically, a particular case illustrated by FIGS. 4 and 5 can be described.

As illustrated in FIG. 4, the median filter FM stores the median values of each subset of the values considered. This eliminates error values. In FIG. 4 for example, the value taken at T−2 is filtered by the median filter FM. This value becomes an indication of a trend towards a change in elevation when the set of values to which the median filter is applied is located around T−2.

For the filtering and sampling steps, such as in the example illustrated in FIG. 5, for clarity the description can be applied in the case of a first buffer B1 containing 11 memory locations. Consider T to be the time referred to below, which corresponds to a clock tick. At time T, the values that were already stored in the first buffer B1 are the values of T−1 to T−10. At this moment a new value collected at time T is stored.

According to a first possibility, the median filter FM is applied at frequency F1 of this base sampling, and in this case an intermediate buffer area denoted B1' is updated with the result of the filtering operation With each clock tick, a new value is obtained from the filtering, for example median filtering, applied to the set of values in the first buffer B1 at time T, meaning to values T to T−10. The new value entered in the intermediate buffer area B1' is a value among the 11 values contained in the first buffer B1 at the time of the clock tick. In the example shown in FIG. 5 this is the value of T−6. The filtered values are denoted 'F-i'.

The second buffer B2, intended in particular for the variance calculation, is filled with the subsampled filtered values, with a clock frequency F2.

In the case illustrated in FIG. 5 we have K=3, therefore one value out of three is sampled. With each sampled value, meaning every third value in the example shown, the value is retained and stored in the buffer B2. In the example shown in FIG. 5, the new filtered value at the clock tick is not the third, so it is not retained in the sample.

At the next clock tick, meaning at time T+1, a new value enters the first buffer B1 and the value collected at T−10 is removed, in the case considered in the example illustrated in FIG. 5. The median filter FM applied to the set of values in the first buffer B1 at time T+1 selects a value among the 11 values in the first buffer B1 at time T+1. In the example illustrated in FIG. 5, this is, for example, the value collected at T−8 in the first buffer B1. In the example illustrated in FIG. 5, the new filtered value corresponds to the third value collected at the sampling frequency. The filtered value at time T+1 is therefore stored in the second buffer B2 and the oldest value stored in the second buffer B2 is deleted (sliding window principle).

Figure 6:
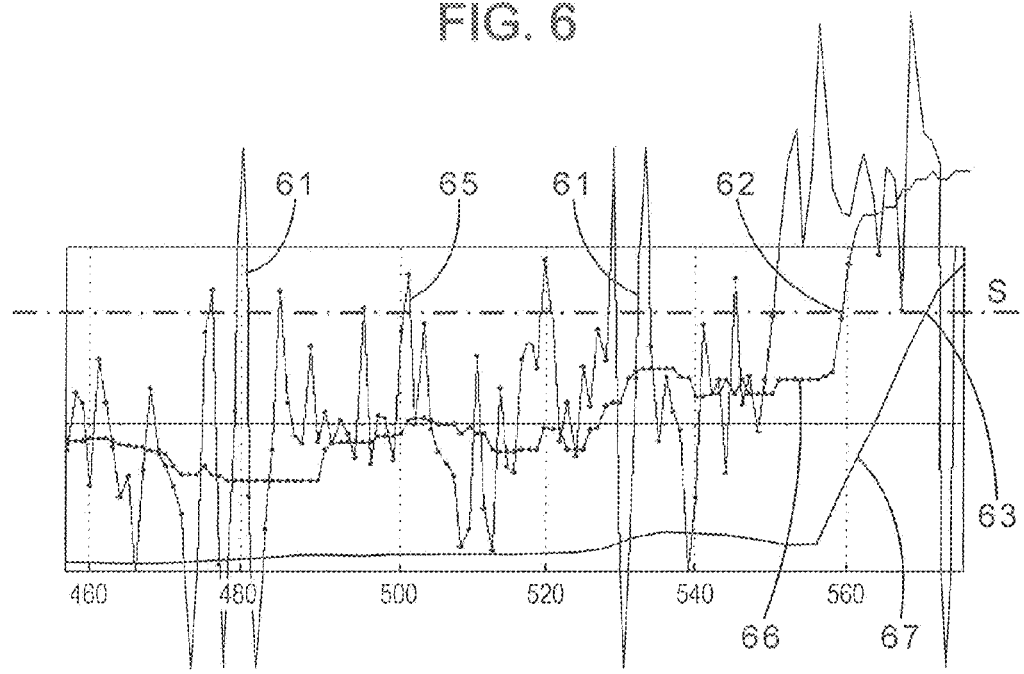
FIG. 6 illustrates a timing diagram of the raw and filtered altitude signals and the variance, FIG. 7 schematically illustrates the method as it progresses.

FIG. 6 illustrates on the same graph the accumulation of detected raw elevation values stored in the first buffer B1 (curve 65), and measured elevation values filtered by the median filter FM then stored in buffer B1' (curve 66). FIG. 6 also shows the variance (curve 67) calculated at certain moments from filtered elevation values, and compared at certain times to the threshold S represented on the same graph. Anomalous values are the values denoted as 61 and they do not impact the variance calculation because they are eliminated by the median filter, and the crossing of the threshold by the variance is denoted by point 63. Note that the crossing of the threshold S lags slightly after the clear increase in elevation at about time 560 (point 62). The developer is free to choose the multiple K between the first frequency F1 and the second frequency F2. However, this choice involves a tradeoff between the real-time aspects of the result, and the false positive rate. For example, if the developer chooses to store one filtered value out of every two, the real-time aspect will be strong but the false positive rate will be non-zero although low, whereas if the developer chooses to store one filtered value out of four, the real-time aspect will be weak but the false positive rate will be almost zero.

The aim of this technique is to extract true elevation changes from the filtered signal, at the best detection rate and with a false detection rate of close to 0%. The strength of the detection algorithm proposed here is that the user can choose the minimum slope to be observed, as well as the false detection rate. For the same value of the threshold S, the more the stored signal is subsampled the greater the minimum slope that can be observed and the lower the false detection rate. The detection threshold S is therefore determined in relation to a minimum slope that serves as a baseline, and the false detection rate desired by the user. Therefore the greater the distance between the samples used, the higher the detection threshold S, which allows for a more definite difference between true and false elevation changes. But the distance between consecutive values cannot be too high in order to maintain the real time aspect.

Figure 7:

FIG. 7 illustrates the set of steps in the method.

Advantageously, the anomalous values in the set of values actually measured are therefore eliminated by the filter. But the use of a median filter FM introduces a delay in observing a change in elevation. When the raw readings collected are tending to shift upward for example, several new data captures will be required before the median values are equivalently shifted. However, the oldest value stored in buffer B2 helps prevent any loss of information concerning the actual elevation change traveled by the user.

Note that the use of the intermediate buffer B1' is not mandatory; the storage capacity of this buffer B1' is not necessarily the same as that of the first buffer B1: it may be very small, for example limited to two or three memory locations.

The invention claimed is:

1. A method for estimating the elevation change traveled by a user, said method using a device comprising at least one pressure sensor configured to provide pressure values, an accelerometer configured to detect accelerations experienced by the device and a temperature sensor configured to provide temperature values in order to adjust the pressure values, said method comprising:
   a)—periodically sampling the pressure values, reading the current pressure at a first sampling frequency F1, and storing the pressure values in the form of pressure or the corresponding altitude in a first buffer,
   b)—filtering the pressure values stored in the first buffer, in order to determine filtered values,
   c)—calculating a variance, on at least a portion of the filtered values, in order to determine a condition for including elevation changes corresponding to observed differences in the stored pressure or altitude values,
   d)—calculating an elevation change traveled for the user, during his/her displacement,
   e)—making a meter of positive elevation gains, based on the elevation change traveled calculation, and
   f)—displaying the meter on a display of the device or communicating the meter to a smartphone.

2. The method according to claim 1, wherein the filtering operation is performed at the rate of the first sampling frequency F1.

3. The method according to claim 1, wherein the variance calculation is performed at a second frequency F2 that is less than or equal to the first sampling frequency F1.

4. The method according to claim 3, wherein the first frequency F1 is a multiple of the second frequency F2, meaning F1=k F2.

5. The method according to claim 1, wherein the variance calculation is performed on P subsampled filtered values stored in a second buffer.

6. The method according to claim 1, further comprising:
comparing the result of the variance calculation VAR to a predetermined threshold value S, and
if VAR>S then the condition for including is 'true' and the observed elevation changes are included in the elevation change traveled calculation, and
if VAR<S then the condition for including is 'false' and the observed elevation changes are not included in the elevation change traveled calculation.

7. The method according to claim 6, wherein, when the condition for including changes from 'false' to 'true', the included observed elevation change is based on the oldest value stored in the second buffer.

8. A device configured to estimate an elevation change traveled by a user, said device comprising at least one pressure sensor configured to provide pressure values, an accelerometer configured to detect accelerations experienced by the device and a temperature sensor configured to provide temperature values in order to adjust the pressure values, said device further configured to:
 a)—perform periodically sampling the pressure values, read the current pressure at a first sampling frequency F1, and store the pressure values in the form of pressure or the corresponding altitude in a first buffer,
 b)—perform a filtering operation on the pressure values stored in the first buffer, in order to determine filtered values,
 c)—perform a variance calculation, on at least a portion of the filtered values, in order to determine a condition for including elevation changes corresponding to observed differences in the stored pressure or altitude values,
 d)—perform an elevation change traveled calculation for the user, during his/her displacement,
 e)—make a meter of positive elevation gains, based on the elevation change traveled calculation, and
 f)—display the meter on a display of the device or to communicate the meter to a smartphone.

9. The device according to claim 8, wherein the device is in the form of a personal activity monitoring unit.

10. The device according to claim 8, further configured to perform the filtering operation at the rate of the first sampling frequency F1.

11. The device according to claim 8, further configured to perform the variance calculation at a second frequency F2 that is less than or equal to the first sampling frequency F1.

12. The device according to claim 11, wherein the first frequency F1 is a multiple of the second frequency F2, meaning F1=k F2.

13. The device according to claim 8, further configured to perform the variance calculation on P subsampled filtered values stored in a second buffer.

14. The device according to claim 8, further configured to:
compare the result of the variance calculation VAR to a predetermined threshold value S,
if VAR>S then the condition for including is 'true' and the observed elevation changes are included in the elevation change traveled calculation,
if VAR<S then the condition for including is 'false' and the observed elevation changes are not included in the elevation change traveled calculation.

15. The device according to claim 14, wherein, when the condition for including changes from 'false' to 'true', the included observed elevation change is based on the oldest value stored in the second buffer.

* * * * *